(12) United States Patent
Choi et al.

(10) Patent No.: US 10,036,000 B2
(45) Date of Patent: Jul. 31, 2018

(54) BETA-GALACTOSIDASE

(71) Applicant: GENOFOCUS CO., LTD., Daejeon (KR)

(72) Inventors: Jae Youl Choi, Daejeon (KR); Jae Gu Pan, Sejong-si (KR); Seung Hwan Park, Daejeon (KR); Eui Joong Kim, Daejeon (KR)

(73) Assignee: GENOFOCUS CO., LTD., Daejeon (KR)

( * ) Notice: Subject to any disclaimer, the term of this patent is extended or adjusted under 35 U.S.C. 154(b) by 0 days.

(21) Appl. No.: 15/313,568

(22) PCT Filed: May 19, 2015

(86) PCT No.: PCT/KR2015/004948
§ 371 (c)(1),
(2) Date: Nov. 23, 2016

(87) PCT Pub. No.: WO2015/178639
PCT Pub. Date: Nov. 26, 2015

(65) Prior Publication Data
US 2017/0198271 A1 Jul. 13, 2017

(30) Foreign Application Priority Data
May 23, 2014 (KR) .......................... 10-2014-0062392

(51) Int. Cl.
| | | |
|---|---|---|
| *C12N 9/38* | (2006.01) | |
| *C12N 9/10* | (2006.01) | |
| *C12P 19/18* | (2006.01) | |
| *C12P 21/06* | (2006.01) | |
| *C12P 19/34* | (2006.01) | |
| *C12N 1/20* | (2006.01) | |
| *C12N 1/00* | (2006.01) | |
| *C07H 21/04* | (2006.01) | |
| *C13K 5/00* | (2006.01) | |
| *C07K 1/00* | (2006.01) | |
| *C12P 19/04* | (2006.01) | |
| *C12P 21/02* | (2006.01) | |

(52) U.S. Cl.
CPC ............ *C12N 9/2471* (2013.01); *C12P 19/04* (2013.01); *C12P 21/02* (2013.01); *C12Y 302/01023* (2013.01)

(58) Field of Classification Search
CPC ........ C12N 9/2471; C12P 19/04; C12P 21/02; C12Y 302/01023

USPC ............ 435/207, 193, 97, 69.1, 91.1, 252.3, 435/254.11; 536/23.1, 23.2, 123.13; 530/350

See application file for complete search history.

(56) References Cited

U.S. PATENT DOCUMENTS 8,288,143 B2 * 10/2012 Stougaard ............ A23C 9/1206
435/207
2012/0135468 A1 5/2012 Katase et al.

FOREIGN PATENT DOCUMENTS

| EP | 0307247 B1 | 8/1994 |
| JP | H09-313177 A | 12/1997 |
| KR | 10-2007-0122102 A | 12/2007 |
| KR | 10-1121161 B1 | 3/2012 |
| WO | 9108291 A2 | 6/1991 |

OTHER PUBLICATIONS

Ito, Y., et al., "Cloning and Characterization of the Gene Encoding a Novel b-Galactosidase from Bacillus circulans", "Bioscience, Biotechnology, and Biochemistry", 1997, pp. 1270-1276, vol. 61, No. 8.
Bultema, J. B., et al., "Biochemical characterization of mutants in the active site residues of the b-galactosidase enzyme of Bacillus circulans ATCC 31382", "FEBS Open Bio", Nov. 2014, pp. 1015-1020, vol. 4.
Definition: BgaM [Bacillus bataviensis LMG 21833], GenBank [online], Oct. 23, 2012, Accession No. EKN65202.1; https://www.ncbi.nlm.nih.gov/protein/409928079/.
Song, J., et al., "Cloning and Expression of a b-Galactosidase Gene of Bacillus ciruclans", "Bioscience, Biotechnology, and Biochemistry", Jun. 13, 2011, pp. 1194-1197, vol. 75, No. 6.
Warmerdam, A., et al., "Characterization of b-Galactosidase Isoforms from Bacillus circulans and Their Contribuition to GOS Production", "Applied Biochemistry and Biotechnology", Mar. 23, 2013, pp. 340-358, vol. 170.

* cited by examiner

*Primary Examiner* — Ganapathirama Raghu
(74) *Attorney, Agent, or Firm* — Hultquist, PLLC; Steven J. Hultquist

(57) ABSTRACT

The present invention relates to a novel beta-galactosidase, and more particularly to a novel beta-galactosidase derived from *Bacillus circulans*, a gene encoding the beta-galactosidase, a recombinant vector and a recombinant microorganism, which contain the gene, a method for producing a beta-galactosidase using the recombinant microorganism, and a method for producing galactooligosaccharide using the beta-galactosidase. The use of the novel beta-galactosidase according to the present invention makes it possible to efficiently produce a large amount of galactooligosaccharide.

6 Claims, 2 Drawing Sheets
(2 of 2 Drawing Sheet(s) Filed in Color)

ated 212 kDa beta-galactosidase I, 145 kDa beta-galactosidase II, and 86 kDa beta-galactosidase III. The nucleotide sequences of the three isoform genes were identified by Amano for beta-galactosidase I (WO2010/140435), GenoFocus for beta-galactosidase II (Korean Patent No. 1,121,161), and the Ito group for beta-galactosidase III. It was found that among the three isoforms, beta-galactosidase I and II can be used for synthesis of galactooligosaccharides. Until now, various research groups have reported that only three beta-galactosidase genes are present in *Bacillus circulans*.

BETA-GALACTOSIDASE

CROSS-REFERENCE TO RELATED APPLICATIONS

This application is a U.S. national phase under the provisions of 35 U.S.C. § 371 of International Patent Application No. PCT/KR15/04948 filed May 19, 2015, which in turn claims priority of Korean Patent Application No. 10-2014-0062392 filed May 23, 2014. The disclosures of such international patent application and Korean priority patent application are hereby incorporated herein by reference in their respective entireties, for all purposes.

TECHNICAL FIELD

The present invention relates to a novel beta-galactosidase, and more particularly to a novel beta-galactosidase derived from *Bacillus circulans*, a gene encoding the beta-galactosidase, a recombinant vector and a recombinant microorganism, which contain the gene, a method for producing a beta-galactosidase using the recombinant microorganism, and a method for producing galacto-oligosaccharide using the beta-galactosidase.

BACKGROUND ART

β-galactosidases hydrolyze non-reducing terminal β-D-galactose in β-D-galactopyranosides such as lactose, or catalyze the transition of β-D-galactopyranoside to galactose. Generally, such enzymes have two characteristics (hydrolytic activity and transglycosylation activity) which are all industrially applicable. The hydrolytic activity hydrolyzes lactose in milk and milk products to prevent lactose intolerance and increase sweetness, and the transglycosylation activity is used for production of galactooligosaccharides which promote the growth of lactic acid bacteria that are human intestinal beneficial microorganisms.

Beta-galactosidases are found in various microorganisms, plants and animals, but beta-galactosidases which are currently used in industrial applications are those isolated from microorganisms. Bata-galactosidases having different transglycosylation specificities were isolated from *Bacillus* sp., *Aspergillus* sp., *Saccharomyces* sp., etc., and various studies on thermostable enzymes have been conducted.

Beta-galactosidases which are currently used for production of galactooligosaccharides in the world are mostly those derived from *Bacillus* sp. or *Aspergillus* sp. Particularly, beta-galactosidases derived from *Bacillus* sp., particularly *Bacillus circulans*, are most frequently used for commercial purposes due to their activation temperature (50 to 60° C.) and high transglycosylation activity. Particularly, a beta-galactosidase derived from *Bacillus circulans* ATCC 31382 is commercially available under the trade name of BIO-LACTA (Amano) This enzyme is known to be produced by culturing *Bacillus circulans* in a suitable medium, followed by cell disruption or recovery from the medium.

The characteristics of the beta-galactosidase derived from *Bacillus circulans* ATCC 31382 were reported in several publications. It was reported that the microorganism *Bacillus circulans* ATCC 31382 contains three structural isoforms of beta-galactosidases. According to the sizes thereof, the beta-galactosidase proteins are designated 212 kDa beta-galactosidase I, 145 kDa beta-galactosidase II, and 86 kDa beta-galactosidase III. The nucleotide sequences of the three isoform genes were identified by Amano for beta-galactosidase I (WO2010/140435), GenoFocus for beta-galactosidase II (Korean Patent No. 1,121,161), and the Ito group for beta-galactosidase III. It was found that among the three isoforms, beta-galactosidase I and II can be used for synthesis of galactooligosaccharides. Until now, various research groups have reported that only three beta-galactosidase genes are present in *Bacillus circulans*.

The present inventors expected that, if beta-galactosidase isoforms are present in *Bacillus circulans*, a beta-glycosidase gene having the characteristics of another additional beta-galactosidase different from the three beta-galactosidases identified to date can be present *Bacillus circulans*. Based on this expectation, the present inventors have made extensive efforts to identify a novel beta-galactosidase, and as a result, have found that a novel beta-galactosidase different from the three reported beta-galactosidases is present in *Bacillus circulans*, and have identified the nucleotide sequence of a gene encoding the novel beta-galactosidase, thereby completing the present invention.

DISCLOSURE OF INVENTION

Technical Problem

It is an object of the present invention to provide a novel beta-galactosidase derived from *Bacillus circulans*.

Another object of the present invention is to provide a gene encoding the novel beta-galactosidase.

Still another object of the present invention is to provide a recombinant vector that contains the above-described gene, and a recombinant microorganism having introduced therein the above-described gene or the above-described recombinant vector.

Yet another object of the present invention is to provide a method for producing a novel beta-galactosidase using the above-described recombinant microorganism.

A further object of the present invention is to provide a method for producing galactooligosaccharide using the above-described novel beta-galactosidase.

Technical Solution

To achieve the above object, the present invention provides a beta-galactosidase having an amino acid sequence of SEQ ID NO: 1.

The present invention also provides a gene that encodes the above-described beta-galactosidase and a recombinant vector comprising the above-described gene.

The present invention also provides a recombinant microorganism wherein the above-described gene or the above-described recombinant vector is introduced into a host cell selected from the group consisting of bacteria, fungi, and yeasts.

The present invention also provides a method for producing a beta-galactosidase, comprising the steps of: culturing the above-described recombinant microorganism to produce a beta-galactosidase; and recovering the produced beta-galactosidase.

The present invention also provides a method for producing a galactooligosaccharide, comprising the steps of: reacting the above-described beta-galactosidase with a lactose-containing substrate to produce galactooligosaccharide; and recovering the produced galactooligosaccharide.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

BEST MODE FOR CARRYING OUT THE INVENTION

Unless defined otherwise, all technical and scientific terms used herein have the same meaning as commonly understood by one of ordinary skill in the art to which the invention pertains. Generally, the nomenclature used herein and the experiment methods, which will be described below, are those well known and commonly employed in the art.

In one aspect, the present invention is directed to a beta-galactosidase having an amino acid sequence of SEQ ID NO: 1 and to a gene encoding the beta-galactosidase.

In the present invention, it was expected that a beta-glycosidase gene having the characteristics of another additional beta-galactosidase different from the three beta-galactosidases identified to date can be present Bacillus circulans. Based on this expectation, a novel beta-galactosidase gene was isolated from the genome of Bacillus circulans.

In an example of the present invention, the genomic DNA of Bacillus circulans ATCC 31382 was digested with each of 23 restriction enzymes to construct a genomic library for beta-galactosidase cloning, and a strain having beta-galactosidase activity was selected from the library.

A Bacillus circulans genomic fragment contained in the selected strain having beta-galactosidase activity was sequenced. As a result, it was found that the fragment contains a beta-galactosidase gene having a novel sequence, in addition to the known beta-galactosidase genes derived from Bacillus circulans.

Figure 1:
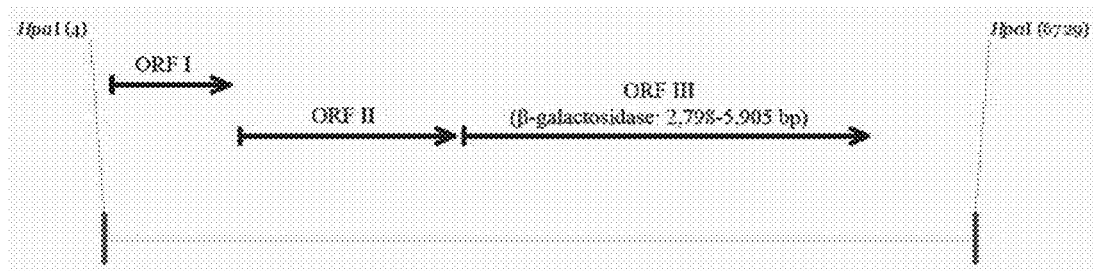
FIG. 1 is a schematic view showing the size and position of the open reading frame (ORF) of a beta-galactosidase gene identified in a fragment obtained by treating the genomic DNA of Bacillus circulans with HpaI restriction enzyme.

The nucleotide sequence of the fragment containing the novel beta-galactosidase gene is represented by SEQ ID NO: 3. The total size of the DNA fragment containing the beta-galactosidase gene was 6731 bp, and three open reading frames (ORFs) were found in the fragment (FIG. 1).

Among these ORFs, the third ORF was found to have a 3105bp DNA size (SEQ ID NO: 2) and to be composed of 1035 amino acid residues (SEQ ID NO: 1) and also to have beta-galactosidase activity.

In another aspect, the present invention is directed to a recombinant vector that contains a gene encoding the beta-galactosidase, and to a recombinant microorganism wherein the gene encoding the beta-galactosidase or the recombinant vector is introduced into a host cell selected from the group consisting of bacteria, fungi, and yeasts.

As used herein, the term "vector" means a DNA construct containing a DNA sequence operably linked to a suitable control sequence capable of effecting the expression of the DNA in a suitable host. The vector may be a plasmid, a phage particle, or simply a potential genomic insert. Once incorporated into a suitable host, the vector may replicate and function independently of the host genome, or may in some instances, integrate into the genome itself. In the present specification, "plasmid" and "vector" are sometimes used interchangeably, as the plasmid is the most commonly used form of vector. However, the present invention is intended to include other types of vectors with the same function as that would be known or known in the art. Typical expression vectors for mammalian cell culture expression are based on, for example, pRK5 (EP 307,247), pSV16B (WO91/08291), and pVL1392 (Pharmingen).

As used herein, the term "expression control sequence refers to the DNA sequences essential for the expression of the coding sequence operably linked to in a particular host organism. Such control sequences include a promoter for performing transcription, any operator sequence for controlling such transcription, a sequence for encoding a suitable mRNA ribosomal binding site, and a sequence for controlling the termination of transcription and translation. For example, control sequences suitable for prokaryotes include a promoter, an arbitrary operator sequence, and a ribosomal binding site. Eukaryotic cells include promoters, polyadenylation signals, and enhancers. The factor having the greatest effect on the expression level of the gene in the plasmid is a promoter. SRαpromoter, cytomegalovirus promoter and the like are preferably used as a promoter for high expression.

To express the DNA sequence of the present invention, any of a wide variety of expression control sequences may be used in the vector. Examples of useful expression control sequences include, for example, the early and late promoters of SV40 or adenovirus, the lac system, the trp system, the TAC or TRC system, T3 and T7 promoters, the major operator and promoter regions of phage lambda, the control regions of fd coat protein, the promoter for 3-phosphoglycerate kinase or other glycolytic enzymes, the promoters of acid phosphatase, e.g., Pho5, the promoters of the yeast αmating system, and other sequences known to control the expression of genes of prokaryotic or eukaryotic cells or their viruses, and various combinations thereof. T7 RNA polymerase promoter Φ010 may be effectively used to express the protein NSP in E. coli.

A nucleic acid sequence is operably linked when it is arranged in a functional relationship with another nucleic acid sequence. The nucleotide sequence may be a gene and a control sequence(s) linked to be capable of expressing the gene when it binds to a control sequence(s) (e.g., transcription-activating protein). For example, DNA for a pre-sequence or a secretory leader is operably linked to DNA encoding polypeptide when expressed as pre-protein participating in secretion of polypeptide; a promoter or an enhancer is operably linked to a coding sequence when affecting the transcription of the sequence; and a RBS is operably linked to a coding sequence when affecting the transcription of the sequence, or to a coding sequence when arranged to facilitate translation. Generally, the term "operably linked" means that the DNA linked sequences are contiguous, and in the case of the secretory leader, are contiguous and present in a reading frame. However, an enhancer is not necessarily contiguous. The linkage between these sequences is performed by ligation at a convenient restriction enzyme site. However, when the site does not exist, a synthetic oligonucleotide adaptor or a linker is used according to a conventional method.

The term expression vector used herein generally means a double-stranded DNA fragment functioning as a recombinant carrier into which a heterologous DNA fragment is inserted. Here, the heterologous DNA means a hetero-type DNA, which is not naturally found in a host cell. The expression vector may be self-replicable regardless of host chromosomal DNA once in a host cell, and may produce several copies of the vector and (heterologous) DNA inserted thereinto.

As is well known in the art, in order to increase the expression level of a transfected gene in a host cell, a corresponding gene should be operably linked to transcription and translation expression control sequences which are operated in a selected expression host. Preferably, the expression control sequences and the corresponding gene are included in one expression vector together with a bacterial selection marker and a replication origin. When an expression host cell is a eukaryotic cell, an expression vector should further include an expression marker which is useful in a eukaryotic expression host.

The host cell transformed or transfected by the aforementioned expression vector constitutes another aspect of the present invention. As used herein, the term "transformation" means that DNA can be replicated as a factor outside of chromosome or by means of completion of the entire chromosome by introducing DNA as a host. As used herein, the term "transfection" means that an expression vector is accepted by a host cell regardless of whether or not any coding sequence is actually expressed.

It should be understood that all vectors and expression control sequences do not equally function in expressing the DNA sequence of the present invention. Similarly, all hosts do not equally function for an identical expression system. However, those skilled in the art may make a suitable selection from among various vectors, expression control sequences, and hosts without either departing from the scope of the present invention or bearing an excessive experimental burden. For example, a vector must be selected taking a host cell into consideration, because the vector should be replicated in the host cell. Specifically, the copy number of a vector, the ability to control the copy number, and the expression of other protein encoded by the vector (e.g., the expression of an antibiotic marker) should also be deliberated. Also, an expression control sequence may be selected taking several factors into consideration. For example, relative strength, control capacity and compatibility with the DNA sequence of the present invention of the sequence should be deliberated particularly with respect to possible secondary structures. Further, the selection of a host cell may be made under consideration of compatibility with a selected vector, toxicity of a product encoded by a DNA sequence, secretory nature of the product, ability to correctly fold a polypeptide, fermentation or cultivation requirements, ability to ensure easy purification of a product encoded by a DNA sequence, or the like. Within the scope of these parameters, one of ordinary skill in the art may select various vectors/expression control sequences/host combinations that can express the DNA sequences of the invention in either large scale animal culture or fermentation. In cloning the cDNA of an NSP protein by the expression cloning strategy, screening procedures such as a binding method, a panning method, and a film emulsion method can be used.

In the definition of the present invention, the term "substantially pure" means that a polypeptide according to the present invention and the DNA sequences encoding the polypeptide substantially do not contain any other proteins derived from bacteria.

As host cells for expressing recombinant proteins, prokaryotic cells, such as *E. coli* and *Bacillus subtillis*, which can be cultured at a high concentration within a short time, easily genetically modified and have well established genetic and physiological properties, have been widely used. However, to solve various problems, including the post-translational modification, secretion, three-dimensional active structure and activation of proteins, a wide range from microorganisms to higher organisms, including unicellular eukaryotic cells, yeasts (*Pichia pastoris, Saccharomyces cerevisiae, Hansenula polymorpha*, etc.), filamentous fungi, insect cells, plant cells, and mammalian cells, has recently been used as host cells for recombinant protein production. Thus, it will be obvious to one skilled in the art to use not only *E. coli* cells illustrated in Examples, but also other host cells.

In still another aspect, the present invention is directed to a method for producing a beta-galactosidase, comprising the steps of: culturing the recombinant microorganism to produce a beta-galactosidase; and recovering the produced beta-galactosidase.

Figure 2:
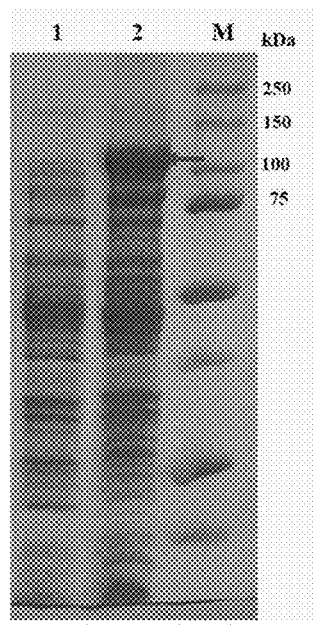
FIG. 2 shows the results of SDS-PAGE performed to analyze the protein expression pattern of a recombinant beta-galactosidase produced in E. coli DH5α/pACE-BgaI.New transformed with the recombinant beta-galactosidase gene. M: protein size marker; 1: DH5α/None; 2: DH5α/pACE-BgaI.New; arrow: beta-galactosidase.

In an example of the present invention, a recombinant beta-galactosidase was produced using transformed recombinant *E. coli* (DH5α/pACE-BgaI.New). Herein, the pACE vector (GenoFocus, Korea) makes it possible to produce a recombinant protein by microbial culture without having to add a separate inducer for protein expression in a state in which cell growth and protein expression are separated from each other. The beta-galactosidase produced by the above-described method was analyzed by SDS-PAGE, and as a result, a band having a size of 120 kDa was observed (FIG. 2).

In another example of the present invention, using the obtained recombinant beta-galactosidase and 4-nitrophenyl-β-D-galactopyranoside (SIGMA) as a substrate, the optimum temperature of an enzymatic reaction was determined.

As a result, it was found that the optimum temperature for activity of the novel beta-galactosidase of the present invention is 40° C.

In yet another aspect, the present invention is directed to a method for producing a galactooligosaccharide, comprising: reacting the beta-galactosidase with a lactose-containing substrate to produce galactooligosaccharide; and recovering the produced galactooligosaccharide.

In the present invention, the galactose oligosaccharide may be one ingredient selected from the group consisting of liquid milk, dried milk powder, baby milk, baby formula, ice cream, yoghurt, cheese, fermented dairy products, beverages, infant foods, cereals, bread, biscuits, confectionary, cakes, food supplements, dietary supplements, probiotic comestible foods, prebiotic comestible foods, animal feeds, poultry feeds, and drugs.

In another example of the present invention, the ability of the novel beta-galactosidase of the present invention to synthesize galactooligosaccharide was analyzed using lactose as a substrate, and as a result, it was shown that the rate of conversion of lactose to galactooligosaccharide by the beta-galactosidase of the present invention was about 32%.

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1

Cloning of Novel Beta-Galactosidase Derived from *Bacillus circulans*

*Bacillus circulans* ATCC 31382 was cultured in LB basal medium (1% tryptone, 0.5% yeast extract, 1% NaCl), and 500 μg of genomic DNA was isolated from the cultured cells by a genomic DNA extraction kit (RBC). The isolated genomic DNA was treated with each of 23 restriction enzymes, AatII, AflII, ApaI, ApaLI, BamHI, BgalII, BsiWI, ClaI, EcoRI, EcoRV, HindIII, HpaI, KpnI, MluI, NcoI, NdeI, NheI, NotI, NsiI, PciI, PsiI, PstI, PvuI, PvuII, SadI, SalI, ScaI, SpeI, SphI, StuI, XbaI, XhoI, and XmaI, and a mixture of 1-8 kb DNA fragments among the DNA fragments obtained by digestion with the restriction enzymes was treated with Klenow fragment enzyme (TaKaRa) to make both ends of the DNA fragments blunt. Then, each of the blunt-end DNA fragments was ligated into a T-blunt vector (SolGent), thereby constructing a library containing each vector, named T-gDNA.flag.

The library was transformed into *E. coli* DH5α which was then cultured in X-gal-containing LB agar (1% tryptone, 0.5% yeast extract, 1% NaCl, 1.5% agar, 50 ug/ml X-gal). After 24 hours, among the transformed *E. coli* colonies grown in the LB agar, colonies showing a green color after degradation of the X-gal were determined to be strains containing a gene having beta-galactosidase activity and were recovered. Each of the recovered colonies was cultured in LB liquid medium, and plasmid vectors were recovered from these colonies by plasmid mini extraction kit (Bioneer) and sequenced (SolGent).

As a result, the nucleotide sequences of several beta-galactosidase genes reported in the prior art were found, and a novel beta-galactosidase gene was found in the vector library produced by treatment with HpaI restriction enzyme.

The nucleotide sequence of the fragment containing the novel beta-galactosidase gene is represented by SEQ ID NO: 3. The total size of the DNA fragment containing the beta-galactosidase gene was 6731 bp, and three open reading frames (ORFs) were found in the fragment (FIG. 1).

Among these ORFs, the third ORF was found to have a 3105bp DNA size (SEQ ID NO: 2) and to be composed of 1035 amino acid residues (SEQ ID NO: 1) and also to have beta-galactosidase activity.

Example 2

Construction of Recombinant Vector and Recombinant Microorganism, Which Contain Beta-Galactosidase II Gene Using the nucleotide sequence of the novel beta-galactosidase from *Bacillus circulans*, obtained in Example 1, a recombinant vector and a recombinant microorganism were constructed.

Based on the nucleotide sequence of the beta-galactosidase (SEQ ID NO: 2), the following primers of SEQ ID NOs: 4 and 5 were constructed.

```
SEQ ID NO. 4: aaaaatgtcacaattaacgtatga;

SEQ ID NO. 5: aaaactgcagttagtgtaaggtaaatgaat.
```

Using the genomic DNA of *Bacillus circulans* as a template, PCR was performed using the primers of SEQ ID NOs: 4 and 5. The PCR product was purified, and then inserted into the NdeI and PstI restriction enzyme sites of a pACE vector (GenoFocus, Korea) by the NdeI and PstI restriction enzyme sequences inserted in the primers, thereby constructing a vector, named pACE-BgaI.New vector. The constructed vector was transformed into an *E. coli* DH5a strain.

Example 3

Production of Novel Beta-Galactosidase Derived from *Bacillus circulans* by Use of Recombinant Microorganism Using the recombinant *E. coli* (DH5α/pACE-BgaI.New) constructed in Example 2, a recombinant beta-galactosidase was produced. The pACE vector (GenoFocus, Korea) makes it possible to produce a recombinant protein by microbial culture without having to add a separate inducer for protein expression in a state in which cell growth and protein expression are separated from each other. Thus, 5 ml of the transformed recombinant strain, which was previously sufficiently seed-cultured, was inoculated into a 1-L Erlenmeyer flask containing 100 ml of sterile LB medium (1% tryptone, 0.5% yeast extract, 1% NaCl) and was cultured at 30° C. and 200 rpm for 24 hours. After completion of the culture, the transformed recombinant strain was separated from the medium by centrifugation and diluted in sterile distilled water at a suitable concentration. The transformed recombinant strain was disrupted with an ultrasonic homogenizer (VibraCell), and then beta-galactosidase II was separated from the cell debris by centrifugation and analyzed by protein electrophoresis (SDS-PAGE).

As a result, as shown in FIG. 2, a beta-galactosidase band having a size of about 120 kDa was observed.

Example 4

Determination of Optimum Temperature for Activity of Novel Beta-Galactosidase

The optimum temperature for activity of the recombinant beta-galactosidase obtained in Example 3 was examined To determine the activity of the beta-galactosidase, 4-nitrophenyl-$\beta$-D-galactopyranoside (SIGMA) was dissolved in various buffers and used as a substrate. An enzymatic reaction using the beta-galactosidase and the substrate was performed at a temperature of 30 to 60° C., and then stopped using 10% (w/v) sodium carbonate ($Na_2CO_3$), followed by color development.

To determine the activity of the enzyme, the concentration of O-nitrophenol released was measured by the absorbance at a wavelength of 420 nm. One unit of the beta-galactosidase was determined as the amount of enzyme that released 1 μmol of O-nitrophenol per minute under the above-described conditions.

Figure 3:
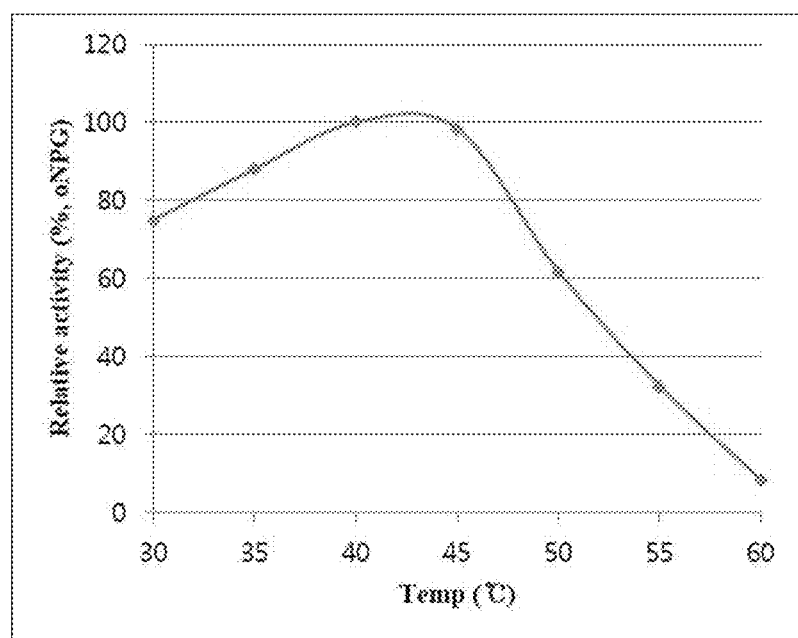
FIG. 3 shows the optimum temperature for activity of a recombinant beta-galactosidase gene produced in transformed E. coli DH5α/pACE-BgaI.New.

As shown in FIG. 3, it was found that the optimum temperature for activity of the beta-galactosidase was 40° C.

Example 5

Synthesis of Oligosaccharide Using Novel Beta-Galactosidase

The galactooligosaccharide-synthesis ability of the beta-galactosidase obtained in Example 3 was analyzed. As a substrate for synthesis of galactooligosaccharide, lactose was used. Lactose was dissolved in 50 mM phosphate buffer (pH 6.0) at a concentration of 500 g/L under a high-temperature condition. 500 ml of the lactose solution (500 g/L concentration) was added to a 1 L reactor, and the reaction temperature was set at 50° C., and the stirring speed was maintained at 100 rpm. The beta-galactosidase was added to the lactose solution until it reached a final concentration of 10 units (U/g lactose). Synthesis of galactooligosaccharide was performed for 48 hours.

The analysis of galactooligosaccharide was performed by HPLC (Agilent) equipped with a RI detector by use of a Polyamine II (YMC) column. As a mobile phase, acetonitrile and purified water were used as a ratio of 65%/35% (v/v). The flow rate of the mobile phase was set at 1.0 ml/min. The results of analysis of galactooligosaccharide after completion of the reaction are shown in Table 1 below.

The rate of conversion to galactooligosaccharide was calculated as follows. The amount described below indicates the peak area measured by HPLC. In the product from the lactose substrate, a di- or higher-order saccharide, except for monosaccharides (glucose and galactose) and disaccharide lactose, is defined as galactooligosaccharide.

Conversion (%) to galactooligosaccharide=[total amount of saccharides]−[amount of glucose]−[amount of galactose]−[amount of lactose]

TABLE 1

| | Saccharide composition | | | | | |
|---|---|---|---|---|---|---|
| | Tetra-saccharide galacto-oligosaccharide | Tri-saccharide galacto-oligosaccharide | Di-saccharide galacto-oligosaccharide | Lactose | Glucose + galactose | Total galacto-oligosaccharide |
| Content (%) | 3.45 | 19.72 | 8.87 | 56.30 | 11.65 | 32.04 |

In Table 1 above, the content (%) is the percentage of each saccharide relative to the sum of total saccharides (glucose, galactose, lactose and oligosaccharide). Thus, it can be seen that the rate of conversion to galactooligosaccharide by the beta-galactosidase of the present invention was about 32%.

INDUSTRIAL APPLICABILITY

The use of the novel beta-galactosidase according to the present invention makes it possible to efficiently produce a large amount of galactooligosaccharide.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A recombinant vector comprising a gene encoding a beta-galactosidase having the amino acid sequence of SEQ ID NO:1.

2. The recombinant vector of claim 1, wherein the gene encoding the beta-galactosidase has the nucleotide sequence of SEQ ID NO:2.

3. A recombinant microorganism wherein a gene having the nucleotide sequence of SEQ ID NO:2 or the recombinant vector of claim 1 or claim 2 is introduced into a host cell selected from the group consisting of bacteria, fungi, and yeasts.

4. A method for producing a beta-galactosidase, comprising the steps of:
culturing the recombinant microorganism of claim 3 to produce a beta-galactosidase; and recovering the produced beta-galactosidase.

5. A method for producing a galactooligosaccharide, comprising:
reacting the beta-galactosidase having the amino acid sequence of SEQ ID NO:1 with a lactose-containing substrate to produce galactooligosaccharide; and recovering the produced galactooligosaccharide.

6. The method of claim 5, wherein the galactooligosaccharide is one ingredient selected from the group consisting of liquid milk, dried milk powder, baby milk, baby formula, ice cream, yoghurt, cheese, fermented dairy products, beverages, infant foods, cereals, bread, biscuits, confectionary, cakes, food supplements, dietary supplements, probiotic comestible foods, prebiotic comestible foods, animal feeds, poultry feeds, and drugs.

* * * * *

UNITED STATES PATENT AND TRADEMARK OFFICE
CERTIFICATE OF CORRECTION

PATENT NO.         : 10,036,000 B2
APPLICATION NO.    : 15/313568
DATED              : July 31, 2018
INVENTOR(S)        : Jae Youl Choi Page 1 of 1

It is certified that error appears in the above-identified patent and that said Letters Patent is hereby corrected as shown below:

In the Specification

Column 7, Line 49: "Sad." should be -- SacI --.

Signed and Sealed this
Fourth Day of September, 2018

Andrei Iancu
*Director of the United States Patent and Trademark Office*

SEQUENCE LISTING

<160> NUMBER OF SEQ ID NOS: 5

<210> SEQ ID NO 1
<211> LENGTH: 1035
<212> TYPE: PRT
<213> ORGANISM: Bacillus circulans

<400> SEQUENCE: 1

```
Met Leu Lys Val Lys Glu Lys Phe Val Tyr Thr Pro Pro Lys Asn Gly
1               5                   10                  15

Tyr Pro Glu Trp Asn Asn Asn Pro Glu Ile Phe Gln Leu Asn Cys Leu
            20                  25                  30

Pro Ala His Ala Thr Ser Met Pro Phe Leu Ser Val Lys Asp Ala Ile
            35                  40                  45

Thr Leu Asp Arg Leu Glu Ser Ser Phe Cys Lys Cys Leu Asn Gly Glu
        50                  55                  60

Trp Lys Phe Ser Phe Ser Glu Asn Pro Ala Asn Arg Asn Pro Asp Phe
65              70                  75                  80

Phe Lys Met Gly Phe Asp Glu Cys Glu Met Lys Pro Ile Gln Val Pro
                85                  90                  95

Ser His Trp Gln Phe Gln Gly Tyr Asp Tyr Pro Gln Tyr Thr Asn Val
            100                 105                 110

Arg Tyr Pro Trp Glu Gly Gln Glu Val Leu Lys Pro Pro Phe Ala Pro
            115                 120                 125

Thr Lys Tyr Asn Pro Val Gly Gln Tyr Ile Thr Tyr Phe Asp Ile Pro
        130                 135                 140

Lys Asp Trp Gly Asp Gln Pro Val Tyr Ile His Phe Ala Gly Val Glu
145             150                 155                 160

Ser Ala Phe Tyr Val Trp Ile Asn Gly Asp Leu Val Gly Tyr Ser Glu
                165                 170                 175

Asp Ser Phe Thr Pro Ser Glu Phe Asp Leu Thr Pro Tyr Leu Val Glu
            180                 185                 190

Gly Thr Asn Lys Leu Ala Val Glu Val Tyr Arg Trp Ser Asp Ala Ser
            195                 200                 205

Trp Leu Glu Asp Gln Asp Phe Trp Arg Leu Ser Gly Ile Phe Arg Asp
        210                 215                 220

Val Tyr Leu Tyr Thr Thr Pro Leu Val His Val Ser Asp Tyr Phe Val
225             230                 235                 240

Arg Thr Asp Leu Asp Glu Asn Tyr Lys Asp Ala Glu Leu Val Val Asn
                245                 250                 255

Met Lys Val Ser Asn Tyr Gly Ser Met Phe Glu Glu Pro Val Thr Ile
            260                 265                 270

Glu Ala His Leu Ile Asp His Thr Gly Tyr Lys Val Phe Ser Glu Val
            275                 280                 285

Met Val Glu Arg His Ile Gln Thr Val Glu Glu Asn Glu Leu Cys Phe
        290                 295                 300

Leu Lys Lys Ile Ser Ser Pro Leu Leu Trp Ser Ala Glu Gln Pro Met
305             310                 315                 320

Leu Tyr Thr Phe Val Ile Thr Val Lys Thr Ile Asp Gly Ser Ile Leu
                325                 330                 335

Glu Ala Gln Ser Cys Lys Val Gly Phe Arg Lys Phe Glu Leu Lys Asp
            340                 345                 350

Gly Leu Met Leu Ile Asn Gly Lys Arg Ile Leu Phe Asn Gly Val Asn
        355                 360                 365
```

-continued

Arg His Glu Phe Ser His Leu Arg Gly Arg Ser Val Thr Lys Glu Asp
370                 375                 380

Met Leu His Asp Val Ile Glu Met Lys Lys His Asn Ile Asn Ala Val
385                 390                 395                 400

Arg Thr Ser His Tyr Pro Asn His Pro Tyr Trp Tyr Asp Leu Cys Asp
            405                 410                 415

Gln Tyr Gly Leu Tyr Val Ile Asp Glu Thr Asn Leu Glu Thr His Gly
            420                 425                 430

Thr Trp Ser Tyr Gly Gln Asn Gln Ile Gln Asn Ala Ile Pro Gly Asp
            435                 440                 445

Lys Glu Glu Trp Thr Ala Asn Val Ile Asp Arg Cys His Ser Met Leu
450                 455                 460

His Arg Asp Lys Asn His Pro Cys Ile Leu Ile Trp Ser Leu Gly Asn
465                 470                 475                 480

Glu Ser Phe Gly Gly Thr Asn Phe Ile Lys Met Lys Asp His Ile Lys
            485                 490                 495

Lys Glu Asp Pro Thr Arg Leu Val His Tyr Glu Gly Val Ala His Tyr
            500                 505                 510

Arg Ala Ser Ser Glu Ala Ser Glu Ile Glu Ser Met Met Tyr Glu His
            515                 520                 525

Pro Ser Lys Leu Glu Ala Tyr Ala Leu Ser Ala Glu Ser Ser Glu Val
530                 535                 540

Pro Leu Lys Pro Tyr Ile Ile Cys Glu Tyr Ala His Ala Met Gly Asn
545                 550                 555                 560

Ser Val Gly Asn Leu Tyr Gln Tyr Thr Asp Leu Phe Asn Lys Tyr Pro
            565                 570                 575

Ile Leu Gln Gly Gly Phe Ile Trp Asp Tyr Lys Asp Gln Ala Ile Gln
            580                 585                 590

Thr Ile Ser Glu Thr Gly Thr Pro Tyr Leu Ala Tyr Gly Gly Asp Phe
            595                 600                 605

Gly Glu Ser Pro Asn Asp Gly Asn Phe Cys Gly Asn Gly Leu Leu Phe
            610                 615                 620

Ala Asp Gly Ser Leu Thr Pro Lys Ile Phe Glu Val Lys Lys Cys Tyr
625                 630                 635                 640

Gln Pro Ile Asp Val Arg Ile Glu His Asp Val Phe Thr Val Ile Asn
            645                 650                 655

Lys His Leu Phe Thr Asp Val Asn Glu Tyr Glu Ala Arg Trp Thr Ile
            660                 665                 670

Leu Lys Asp Gly Glu Glu Ile Ala Ser Glu Ser Ile Ser Ile Ser Cys
            675                 680                 685

Lys Pro Leu Ser Ser Thr Leu Ile Asp Leu Lys Asn Val Leu Ser Lys
            690                 695                 700

Tyr Val Met Asp Asp His Glu Tyr Ile Ile Thr Ile Ser Phe His Thr
705                 710                 715                 720

Val Lys Asp Ser Leu Trp Ala Gln Lys Gly Tyr Glu Ile Ala Phe Asp
            725                 730                 735

Gln Phe Val Leu Thr Asn Arg Ile Ile Ala Gln Arg Val Pro Ser Met
            740                 745                 750

Ser Ile Lys Arg Ile Glu Lys Thr Asn Asp Asn Leu Lys Ile Glu Gly
            755                 760                 765

Glu Thr Phe Ser Val Ile Val Ser Lys Thr Ser Gly Phe Ile Thr Ser
770                 775                 780

Phe Val Lys Gln Gly Val Glu Ile Leu Ala Glu Pro Ile Val Pro Asn

```
                    785                 790                 795                 800
              Phe Trp Arg Ala Leu Thr Asp Asn Asp Arg Gly Asn Lys Leu Gly Glu
                          805                 810                 815

Arg Thr Gly Ile Trp Glu Gln Ala Gly Lys Thr Ala Val Leu Gln Gln
                          820                 825                 830

Met Asp Val Glu Glu Met Asp Lys Thr Val His Ile Lys Thr Val Leu
                          835                 840                 845

Gln Leu Gln Thr Ser Pro Ala Ser Val Cys Ser Ile Asp Tyr Glu Ile
                  850                 855                 860

Thr Gly Asp Gly Glu Ile His Val Ala Phe Glu Leu Gln Pro Gly Asp
              865                 870                 875                 880

Gly Leu Pro Glu Ile Pro Glu Ile Gly Met Ile Leu Pro Leu Val Lys
                              885                 890                 895

Ser Phe Glu Ala Ile Ser Trp Tyr Gly Lys Gly Pro His Glu Asn Tyr
                          900                 905                 910

Trp Asp Arg Glu Lys Gly Ala Lys Ile Gly Arg Tyr Val Ser Thr Val
                          915                 920                 925

Glu Asn Glu Phe Thr Pro Tyr Leu Lys Pro Gln Glu Asn Gly Asn Lys
                  930                 935                 940

Ile Gly Val Arg Ser Phe Glu Ile Gly Asp Gly Arg Gly Ile Ile Leu
              945                 950                 955                 960

Arg Val Ser Ser Asp Ser Leu Leu Glu Ile Asn Ala Gly Ala Tyr Ser
                              965                 970                 975

Ala Thr Glu Leu Gln Glu Ala Ala His Thr Tyr Gln Leu Pro Glu Arg
                          980                 985                 990

Thr Lys Thr Tyr Leu Arg Val Asn His Lys Gln Met Gly Ile Gly Gly
                  995                 1000                1005

Asp Asp Ser Trp Ala Ala Lys Thr His Pro Glu Phe Thr Leu Tyr
                  1010                1015                1020

Ser Asp His Thr Tyr Gln Tyr Ser Phe Thr Leu His
                  1025                1030                1035

<210> SEQ ID NO 2
<211> LENGTH: 3108
<212> TYPE: DNA
<213> ORGANISM: Bacillus circulans

<400> SEQUENCE: 2
atgttaaaag tgaaagaaaa atttgtttat acaccaccta aaaacgggta tccggagtgg    60
aataataatc cggaaatttt ccagctcaat tgtttgcctg cacatgctac gagtatgccg   120 ttttttgtcgg tgaaagatgc aataacatta gatcgattgg agtcttcgtt ctgtaaatgt   180
ttgaatgggg aatggaaatt ttcatttcca gagaatccgg caaatcgaaa tcctgatttt   240
tttaaaatgg gatttgatga atgtgagatg aaaccgattc aagttccttc ccattggcaa   300
tttcagggct atgattatcc gcagtatacg aatgtccgtt atccatggga agagcaagaa   360
gttttaaagc ctcccttgc accgacaaaa tataatcccg taggtcaata cattacatat   420
tttgatatcc cgaaggattg gggagatcag ccggtatata ttcattttgc agggtggaa    480 tccgcttttt acgtgtggat aaatggcgat ttagttggtt acagtgaaga tagttttact   540
cctagtgagt ttgatctaac tccttattta gtagaaggaa cgaataaact ggcggtagaa   600
gtttatcgct ggagtgatgc cagttggtta gaggaccagg atttttggcg attaagtggt   660
attttcaggg atgtatatct gtataccaca ccgctagtac atgttcggga ttattttgta   720
```

```
cgtacagatc tagatgaaaa ttataaagat gcagaactag ttgtaaatat gaaagtatcg    780
aattatggca gtatgtttga ggagcctgtt actatcgaag cacatttaat tgatcataca    840
ggctacaaag tatttagcga ggttatggta gagcgacata tacaaacagt agaggaaaat    900
gagttatgct ttttaaaaaa aatatcttct cccctcctgt ggagtgcgga gcagccaatg    960
ctttatacat ttgttattac cgtgaaaact atagatggtt cgatattgga agcgcaaagc   1020
tgtaaagtgg gctttcgtaa atttgaatta aaggatggcc tgatgctgat taatggcaaa   1080
aggatattgt ttaacggtgt aaatcgtcat gagttttctc atctgcgcgg tcgctctgtc   1140
acaaaagagg atatgcttca tgatgtcatc gaaatgaaaa agcataatat taatgctgtg   1200
agaacttctc attatccaaa ccatccctat tggtatgatt tatgtgatca atatggttta   1260
tatgtaatcg atgaaactaa tttagaaacg catggtacat ggtcttatgg tcagaatcaa   1320
attcaaaatg ccattccggg agataaggaa gagtggacag ccaatgtgat cgatcgctgt   1380
cattccatgc tgcatcggga taagaatcat ccgtgcattc taatttggtc gctcggaaat   1440
gaatctttcg gcggaaccaa ttttattaaa atgaaagatc atatcaaaaa ggaggaccca   1500
actcgccttg ttcactacga aggggtagcc cattatcgtg cttcaagtga ggcttcggaa   1560
attgaaagta tgatgtacga acatccttca aaactcgaag cctatgccct aagtgcagaa   1620
agcagtgaag tgccgctgaa gccatatatt atttgtgagt atgcacatgc aatggggaat   1680
tctgtaggaa atctctatca atatactgat ctatttaata agtatccaat tttacaggga   1740
ggttttattt gggattataa agatcaagcc attcaaacca tctctgaaac cggaacaccg   1800
tatttagctt atggggggaga ttttggagaa tcgccgaacg acggtaattt ttgcggcaat   1860
ggcctgttat ttgcagatgg gtctttaaca cctaaaatct ttgaagtaaa aaaatgctat   1920
cagccaattg atgtccgaat tgagcatgat gtatttaccg tcatcaataa gcacttattc   1980
actgacgtaa acgaatatga ggcaaggtgg accatactta agatggggga agagattgcg   2040
agtgaaagca taagtatttc ctgtaagccg ctatcatcta cattgataga tcttaaaaat   2100
gtattgtcaa aatatgtaat ggatgatcat gaatatatta taactattag ttttcacact   2160
gttaaagata gcctttgggc tcaaaagggt tatgaaatag cctttgatca atttgttcta   2220
acaaatcgaa tcattgccca gagagtaccg agcatgtcta ttaaacgtat tgaaaagaca   2280
aacgataatt tgaaaattga gggtgaaaca ttctccgtta ttgtaagtaa acatcagga    2340 ttcataactt ctttcgtaaa acagggtgta gagatttag ctgagccaat tgttccgaat    2400
ttctggaggg ctcttaccga taatgaccgt gggaataaat taggtgagcg tacaggaatt   2460
tgggaacagg cgggaaaaac ggccgttttg caacagatgg atgtagagga aatggataaa   2520
acggttcata ttaaaaccgt acttcaatta caaacttcac ctgcttcagt ttgtagtatt   2580
gattatgaaa taactggaga cggagaaatt catgttgcgt ttgaacttca gcctggtgat   2640
gggttgccgg aaattcctga atcgggatg atccctgcctt tagtcaaatc gtttgaggct   2700
atttcttggt acgaaaaagg tcctcatgaa aattattggg accgtgaaaa gggggcaaaa   2760
attggccgct atgtatcgac agtggaaaat gagtttacac catatctaaa accacaagaa   2820
aatgggaata aatcggagt ccgctcgttt gaaattgggg atggccgtgg aataatcctc    2880
cgtgtttcaa gtgattcatt attagaaatt aatgcaggtg cctattcggc aacagaatta    2940
caggaagcag cccatacgta tcagctgcct gaaagaacaa aaacgtattt acgcgtaaac   3000
cataagcaaa tggggattgg cggagatgat tcttgggctg caaagaccca tccggaattc   3060
actttatatt ctgatcatac ttatcaatat tcatttacct tacactaa                3108
```

<210> SEQ ID NO 3
<211> LENGTH: 6731
<212> TYPE: DNA
<213> ORGANISM: Bacillus circulans

<400> SEQUENCE: 3

| | | | | | |
|---|---|---|---|---|---|
| gttaacttca | tattaatctt | tactgctaac | aaaatatcta | aacgattctc atcatcaagc | 60 |
| ttatggtagg | agggaaggat | atgacgaaaa | caggaaatac | aagaattaaa gaatcaaaaa | 120 |
| ttgatcgcct | ttttatagga | gctatttatg | tattttttagt | tctcatttta atagctgttt | 180 |
| tatatccgct | tatctatatt | gtgagcgctt | catttagcag | tgcatctgcg gtaacatccg | 240 |
| ggagtgtttg | gctgtggccg | gtagaaccaa | cactattagg | atacacgaca gtgtttaaga | 300 |
| atccgcaaat | tcttcaaggg | ttttataatt | cgctgtttta | cactgttgtt ggaacctta | 360 |
| ttagtgtaag | tatcacgatt | atgcttgcct | atccgctttc | aagaaaaaca ttttatgggc | 420 |
| gaaaattgat | catgatttta | ctggttttta | cgatgatttt | tgatggggga ttaataccgt | 480 |
| tgtatttggt | tgtaaaaagt | ttgcatttaa | ttgatacaat | atgggcactt ttactcccgt | 540 |
| ccgcattagc | ggttttccaa | gtgattattg | ctagaacatt | cttccaatct acgataccgg | 600 |
| atgaattagt | agaagcaagt | gaaatggatg | gctgcagcga | tattggattc atcctgaaag | 660 |
| ttgtcctgcc | gttgtccaaa | ccgattattg | cagttcttgt | cctcatgtat gcggtgatga | 720 |
| aatggaatat | gtactttgat | gcattgattt | atttgaaatc | cgaagagcta tatccattac | 780 |
| agctcatttt | acgaagcatc | ttaattttga | atactgaccc | atctgcaaat attgaagata | 840 |
| tattgaaaat | gcaaggattg | aaagaattaa | tgaagtactc | attgattgtt atttcaagtt | 900 |
| taccagtttt | ggtgctgtat | ccatttgttc | aaaaacattt | tgtaaaaggc atgttaattg | 960 |
| gatctgtaaa | aggatgaaga | agaagcaatc | cagctaatac | cagaggacgt tagaaaaaat | 1020 |
| aatataacgt | taaacaaaca | aaggagaggg | tcaaatgaaa | aagttatcaa ctagtttcat | 1080 |
| gcttttagtt | ttaatgacga | tgcttttcgc | cggatgtgtt | cctactaaga aagttcatc | 1140 |
| cgaaggttca | aaaagtgaaa | gtccagatcc | aaacggacca | attgaagttt ccattttcac | 1200 |
| cccgagtata | tcgtatgatc | cagttttttga | cagggataaa | aatgaattca caaaaatggt | 1260 |
| tgaagagaaa | tttaatatca | aaattaattg | gcaatttgca | aaccaggatg cagcaaaaga | 1320 |
| aaaacgtcaa | ttgtctctag | ccagcggaga | ctatccagat | gcatatttgc ttgttgcatg | 1380 |
| gttagataat | atttctaaag | tggaagccca | aaagtatggg | aaagaaggtg tatttctgcc | 1440 |
| attaaataat | ttaatagaaa | aacatgcgcc | aaatctccaa | aaattaatga cagaagtccc | 1500 |
| ttatatggaa | aaaggaatga | ctgcaccgga | tggtaatatt | tatgctcttc ctccaatcaa | 1560 |
| tgaatgtttc | cattgttcaa | gatatgggaa | gatgtggata | aatacggact ggttgaaaaa | 1620 |
| attaaattta | gaaatgccta | aaacaacgga | agaatttaaa | acagtattag aagcatttaa | 1680 |
| aaataatgat | ccaaatggaa | acggcaagaa | ggatgaaatc | ccattaagcg gagaaagtac | 1740 |
| catgttaggg | gatgatccaa | cgatcttcct | aatgaatgca | ttttttgccag ataatggtaa | 1800 |
| ggattatata | aatgtacagg | atggaaaatt | agtgttagct | ccgatgcagc cagcttggaa | 1860 |
| agatgggttg | aaatacattc | attctctttta | taaagagggg | ttaatcgatc aaggagcatt | 1920 |
| cacccaaaac | ccggaggcgt | ataagcagtt | aggtactcct | aaagggatg aagtccttgg | 1980 |
| tgctggtgca | gcaagtcatt | tagcaattat | atctgatata | gcttctgaca aatcaaaagc | 2040 |
| attcgatgtt | gtcccaccgt | taaaaggtcc | tgaaggtgct | caatttacac cttctgatta | 2100 |

-continued

```
tggtaatatc aataatttca cgtttgccat tacgaataaa gcaaatggga aaaaagccga    2160
agcattaatt aagttagcag atttcttata tactgaagaa ggaaccatga tgacagctag    2220
aggtaaggaa ggcgttcatt ggaaaaaggg cggtccggat gatattgatt taactggcaa    2280
acaagcaaaa tatgccatca ttcctagcga ccctaacgag aaagaggaag acaaggtaga    2340
atatggctgg ggagaaagag gtcctctggc actaactagg acacttaggg actccattgc    2400
tgcagaaaca gatgagctgt cctcaaaggg ctatgaaaga agattatata atgcaacact    2460
aaaatatgag ggatttgaac cgaaggaaca atttaatttt gaagcggcat gggttgatcc    2520
taaaaaagca gacgaagtga atctgttaaa aatcaatatt aataaataca tccaagaaaa    2580
tcttgttcaa ttcgtgacag gttcaaagaa catcgataaa gactgggata agtacgttga    2640
cggttttaaa gcattacagg ttgaccgcta tctagaaatc tatcaaaaag cgtatgatgt    2700
cggaaagtaa tacttgaaca ttacaaaaaa agaatacact taagtttttat tctggcgtgt    2760 attctttttt cttttgaaaa gggggatgat gtccaatatg ttaaaagtga agaaaaatt    2820 tgtttataca ccacctaaaa acgggtatcc ggagtggaat aataatccgg aaattttcca    2880
gctcaattgt ttgcctgcac atgctacgag tatgccgttt ttgtcggtga agatgcaat    2940 aacattagat cgattggagt cttcgttctg taaatgtttg aatggggaat ggaaattttc    3000
attttcagag aatccggcaa atcgaaatcc tgattttttt aaaatgggat ttgatgaatg    3060
tgagatgaaa ccgattcaag ttccttccca ttggcaattt cagggctatg attatccgca    3120
gtatacgaat gtccgttatc catgggaaga gcaagaagtt ttaaagcctc cctttgcacc    3180
gacaaaatat aatcccgtag gtcaatacat tacatatttt gatatcccga aggattgggg    3240
agatcagccg gtatatattc attttgcagg ggtggaatcc gcttttacg tgtggataaa    3300 tggcgattta gttggttaca gtgaagatag ttttactcct agtgagtttg atctaactcc    3360
ttatttagta gaaggaacga ataaactggc ggtagaagtt tatcgctgga gtgatgccag    3420
ttggttagag gaccaggatt tttggcgatt aagtggtatt ttcagggatg tatatctgta    3480
taccacaccg ctagtacatg tttcggatta ttttgtacgt acagatctag atgaaaatta    3540
taaagatgca gaactagttg taaatatgaa agtatcgaat tatggcagta tgtttgagga    3600
gcctgttact atcgaagcac atttaattga tcatacaggc tacaaagtat ttagcgaggt    3660
tatggtagag cgacatatac aaacagtaga ggaaaatgag ttatgctttt taaaaaaaat    3720
atcttctccc ctcctgtgga gtgcggagca gccaatgctt tatacatttg ttattaccgt    3780
gaaaactata gatggttcga tattggaagc gcaaagctgt aaagtgggct ttcgtaaatt    3840
tgaattaaag gatggcctga tgctgattaa tggcaaaagg atattgttta acggtgtaaa    3900
tcgtcatgag ttttctcatc tgcgcggtcg ctctgtcaca aaagaggata tgcttcatga    3960
tgtcatcgaa atgaaaaagc ataatattaa tgctgtgaga acttctcatt atccaaacca    4020
tccctattgg tatgatttat gtgatcaata tggtttatat gtaatcgatg aaactaattt    4080
agaaacgcat ggtacatggt cttatggtca gaatcaaatt caaaatgcca ttccgggaga    4140
taaggaagag tggacagcca atgtgatcga tcgctgtcat tccatgctgc atcgggataa    4200
gaatcatccg tgcattctaa tttggtcgct cggaaatgaa tctttcggcg gaaccaattt    4260
tattaaaatg aaagatcata tcaaaaagga ggacccaact cgccttgttc actacgaagg    4320
ggtagcccat tatcgtgctt caagtgaggc ttcggaaatt gaaagtatga tgtacgaaca    4380
tccttcaaaa ctcgaagcct atgccctaag tgcagaaagc agtgaagtgc cgctgaagcc    4440
atatattatt tgtgagtatg cacatgcaat ggggaattct gtaggaaatc tctatcaata    4500
```

```
tactgatcta tttaataagt atccaattt acagggaggt tttatttggg attataaaga    4560
tcaagccatt caaaccatct ctgaaaccgg aacaccgtat ttagcttatg ggggagattt    4620
tggagaatcg ccgaacgacg gtaattttg cggcaatggc ctgttatttg cagatgggtc    4680
tttaacacct aaaatctttg aagtaaaaaa atgctatcag ccaattgatg tccgaattga    4740
gcatgatgta tttaccgtca tcaataagca cttattcact gacgtaaacg aatatgaggc    4800
aaggtggacc atacttaaag atggggaaga gattgcgagt gaaagcataa gtatttcctg    4860
taagccgcta tcatctacat tgatagatct taaaaatgta ttgtcaaaat atgtaatgga    4920
tgatcatgaa tatattataa ctattagttt tcacactgtt aaagatagcc tttgggctca    4980
aaagggttat gaaatagcct ttgatcaatt tgttctaaca aatcgaatca ttgcccagag    5040
agtaccgagc atgtctatta aacgtattga aaagacaaac gataatttga aaattgaggg    5100
tgaaacattc tccgttattg taagtaaaac atcaggattc ataacttctt tcgtaaaaca    5160
gggtgtagag attttagctg agccaattgt tccgaatttc tggagggctc ttaccgataa    5220
tgaccgtggg aataaattag gtgagcgtac aggaatttgg aacaggcgg aaaaacggc    5280
cgttttgcaa cagatggatg tagaggaaat ggataaaacg gttcatatta aaaccgtact    5340
tcaattacaa acttcacctg cttcagtttg tagtattgat tatgaaataa ctggagacgg    5400
agaaattcat gttgcgtttg aacttcagcc tggtgatggg ttgccggaaa ttcctgaaat    5460
cgggatgatc ctgcctttag tcaaatcgtt tgaggctatt tcttggtacg aaaaggtcc    5520
tcatgaaaat tattgggacc gtgaaaaggg ggcaaaaatt ggccgctatg tatcgacagt    5580
ggaaaatgag tttacaccat atctaaaacc acaagaaaat gggaataaaa tcggagtccg    5640
ctcgtttgaa attggggatg gccgtggaat aatcctccgt gtttcaagtg attcattatt    5700
agaaattaat gcaggtgcct attcggcaac agaattacag gaagcagccc atacgtatca    5760
gctgcctgaa agaacaaaaa cgtatttacg cgtaaaccat aagcaaatgg ggattggcgg    5820
agatgattct tgggctgcaa agacccatcc ggaattcact ttatattctg atcatactta    5880
tcaatattca tttaccttac actaataaaa aagtagaaat gggagattta ttaaatgaat    5940
ctttaacct ataggaaagc ggcaaaggga tggacagagg ctctccccgct cggaaacggc    6000
agaattggtg caatgcactt cggaggggtg gagacagaac gatttcagtt aaatgaggac    6060
acattgtggt ctggcccgcc gcaaagcaat aaagaataca acgatcaagc atctttaaaa    6120
agggtaaggc agctgctcga tgaagagaaa tacgaagagg ccaatgacga gacaaagaat    6180
atgtttggtc cgtatacaca aagctatatg cctttgggga atttattcat tcaataccag    6240
cacggtgaca cagcacagaa ttatcatcgg acacttgata ttaaagaggc aatctccaat    6300
gtcaaatata ctattggaaa aattgactac acaagggaag cgtttatttc acatccgcat    6360
gaagtattag ctgtccggct gaccagctct gttcccaaac aattaaactt gataatttca    6420
ttggatagct tattaaaata taaaacttcg gatatatctg acgggttagt tttacaaggg    6480
gtttgtcctg aaagatgtga tcctgttat tttcatgaga acgaacagcc tgttatttac    6540
ggtgagtttg gtgaaacaaa agcgattcat tttgagggaa ggctggctgc tgttgttgaa    6600
gatgggcaag tggaatcatc aaaagggaat ctaacgatcc agcatgcaac aacagccgtt    6660
ttatattttt ctgttgcgac atcttttaac gggtttgatc aacttccggg aacagatttc    6720
gaagagttaa c                                                         6731
```

<210> SEQ ID NO 4

```
<211> LENGTH: 24
<212> TYPE: DNA
<213> ORGANISM: Artificial Sequence
<220> FEATURE:
<223> OTHER INFORMATION: primer

<400> SEQUENCE: 4
aaaaatgtca caattaacgt atga                                              24

<210> SEQ ID NO 5
<211> LENGTH: 30
<212> TYPE: DNA
<213> ORGANISM: Artificial Sequence
<220> FEATURE:
<223> OTHER INFORMATION: primer

<400> SEQUENCE: 5
aaaactgcag ttagtgtaag gtaaatgaat                                        30
```